United States Patent
Sun et al.

(10) Patent No.: US 8,277,659 B2
(45) Date of Patent: Oct. 2, 2012

(54) MICROCHIP CAPILLARY ELECTROPHORESIS ABSENT ELECTROKINETIC INJECTION

(75) Inventors: Xuefei Sun, Richland, WA (US); Ryan T. Kelly, West Richland, WA (US); Keqi Tang, Richland, WA (US); Richard D. Smith, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 215 days.

(21) Appl. No.: 12/889,108

(22) Filed: Sep. 23, 2010

(65) Prior Publication Data

US 2012/0074066 A1    Mar. 29, 2012

(51) Int. Cl.
*B01D 15/08* (2006.01)
(52) U.S. Cl. ............... 210/635; 210/656; 210/198.2; 204/452; 204/604
(58) Field of Classification Search ............ 210/635, 210/656, 659, 198.2; 204/452, 604
See application file for complete search history.

(56) References Cited

U.S. PATENT DOCUMENTS

| | | | |
|---|---|---|---|
| 7,128,876 B2 * | 10/2006 | Yin et al. | 422/508 |
| 7,250,128 B2 | 7/2007 | Unger et al. | |
| 7,740,747 B2 * | 6/2010 | Tian et al. | 204/453 |
| 8,182,746 B2 * | 5/2012 | Guzman | 422/82.01 |
| 2002/0121487 A1 * | 9/2002 | Robotti et al. | 210/767 |
| 2004/0209354 A1 * | 10/2004 | Mathies et al. | 435/287.2 |
| 2006/0011548 A1 * | 1/2006 | Yin et al. | 210/656 |
| 2007/0110628 A1 * | 5/2007 | Loboda | 422/100 |
| 2009/0166203 A1 * | 7/2009 | Tian et al. | 204/453 |
| 2010/0116658 A1 * | 5/2010 | Smuc et al. | 204/452 |
| 2012/0074066 A1 * | 3/2012 | Sun et al. | 210/656 |

OTHER PUBLICATIONS

Allen, Peter B., et al., "Fourier Transform Capillary Electrophoresis with Laminar-Flow Gated Pressure Injection", Anal. Chem., Sep. 1, 2007, 6807-6815 pps., vol. 79, USA.
Price, Alexander K., et al., "Generation of Nonblased Hydrodynamic Injections on Microfluidic Devices Using Integrated Dielectric Elastomer Actuators", Anal. Chem., Nov. 1, 2009, 8942-8948 pps., vol. 81, No. 21, Manhattan, Kansas, USA.
Kenata, Takashi, et al., "Hadamard Transform Capillary Electrophoresis", Anal. Chem., Dec. 1, 1999, 5444-5446 pps., vol. 71, No. 23, Japan.
Jacobson, Stephen C., et al., "Effects of Injection Schemes and Column Geometry on the Performance of Microchip Electrophoresis Devices," Anal. Chem., Apr. 1, 1994, 1107-1113 pps., vol. 66, No. 7, Oak Ridge, Tennessee, USA.
Unger, Marc A., et al., "Monolithic Microfabricated Valves and Pumps by Multilayer Soft Lithography," Science, vol. 288, Apr. 7, 2000, 113-116 pps., Pasadena, CA, USA.

* cited by examiner

*Primary Examiner* — Ernest G Therkorn
(74) *Attorney, Agent, or Firm* — Allan C. Tuan

(57) ABSTRACT

Microchip capillary electrophoresis (CE) utilizing a sample injector based on a mechanical valve rather than electrokinetic injection can provide improved sample injections, enhanced capabilities, and can eliminate the need for changing the electric field in the separation channel to induce sample injection. In one instance CE electrodes continuously apply an electric field for CE separation along a separation channel. A sample channel is connected to the separation channel at an intersection and has a sample pressure that is greater than that which is present in the separation channel near the intersection. The sample channel does not have electrodes that apply voltages for electrokinetic injection. A sample injector in the sample channel or at the intersection comprises a mechanical valve to control sample injection from the sample channel to the separation channel.

4 Claims, 10 Drawing Sheets

MICROCHIP CAPILLARY ELECTROPHORESIS ABSENT ELECTROKINETIC INJECTION

STATEMENT REGARDING FEDERALLY SPONSORED RESEARCH OR DEVELOPMENT

The invention was made with Government support under grant number RR018522 from the U.S. National Institutes of Health and contract DE-AC05-76RL01830 awarded by the US Department of Energy. The government has certain rights in the invention.

BACKGROUND

When performing microchip capillary electrophoresis (CE), sample introduction and injection can significantly affect CE performance. Currently, electrokinetic injection is used almost exclusively for microchip CE sample injection. In a particular type of electrokinetic injection known as "pinched" injection, various electrodes in a first mode apply voltages in four intersecting channels to drive sample through the intersection to a waste reservoir. In a second mode, the voltages induce injection of only a plug of sample occupying the small volume in the intersection towards a separation channel. The voltage applied to the separation channel is different in the first mode, wherein sample is diverted to waste, compared to the second mode, wherein the plug of sample is injected into the separation channel. Except for the sample plug, the vast majority of sample is wasted.

While electrokinetic injection can yield small sample plugs for improved separation efficiency and can minimize electrophoretic injection bias under certain conditions, it also has several significant limitations. For example, a considerable amount of time is required to achieve steady state in the first mode. Steady state is a necessary condition to avoid sample bias and/or injection bias caused by high mobility species arriving more quickly than low mobility species. During prolonged operation, the high mobility species can be depleted preferentially and prematurely from the sample supply. Sample utilization is extremely inefficient because the total volume required is very large compared to the actual injected plug volume, which is very small. Furthermore, the injection volume is fixed because it is determined by the geometry of the intersection. In order to change the injection volume, the geometry of the intersection must typically be altered. Further still, the rate at which sequential injections can be analyzed, and the total number of sample plugs that can be injected into the separation channel, is limited by the steady-state flow requirements and by the changing voltages in the separation channel associated with electrokinetic injection.

In view of at least the limitations described above, a need for an improved sample injector and microchip CE system exists.

SUMMARY

The present invention is a microchip CE system that utilizes a sample injector based on a mechanical valve rather than electrokinetic injection. The mechanical valve can be operated to provide rapid sequential sample injections and to eliminate the need for changing the electric field in the separation channel to induce sample injection. Instead, sample injection is accomplished by pressure gradients and by opening the mechanical valve. A constant electric field can, therefore, be continuously applied along the separation channel. Varying the sample pressure and/or the duration of time that the valve remains in an open position can vary sample injection volume. Preferably mass spectrometry is performed to analyze the sample after CE separation.

In one embodiment, the microchip CE system comprises a separation channel and CE electrodes continuously applying an electric field for CE separation along the separation channel. As used herein, the continuous application of an electric field along the separation channel for CE separation is significant because any sample injection provided to the separation channel will be subject to a continuously applied CE separation field. There is no required change in voltage between an injection mode and a CE separation mode.

A sample channel is connected to the separation channel at an intersection and has a sample pressure that is greater than that which is present in the separation channel near the intersection. The sample channel does not have electrodes that apply voltages for electrokinetic injection. A sample injector in the sample channel, or at the intersection, comprises a mechanical valve to control sample injection from the sample channel to the separation channel. When the valve is opened for a short time, a small volume of sample solution is pushed into the separation channel under a low pressure. When the valve is closed, the sample solution is completely isolated from the CE run buffer in the separation channel such that there is no risk of sample leakage during the operation, and a discrete, well defined sample plug is injected with each valve opening event.

A significant characteristic of the system is that the sample injection is independent of the CE separation. During operation, a high voltage is applied only along the separation channel and no voltage switching is needed. The sample is directly provided into the separation channel for subsequent CE separation. There is no need to wait for production of a steady-state, stable sample plug as would be required in the traditional electrokinetic injection. Discrete sample plugs can be injected repeatedly over relatively long periods of time. The injection and separation frequency is only determined by the actuation of the mechanical valve. A valve having a high duty cycle makes it possible to perform continuous flow monitoring, high throughput analysis, and/or multiplexed separations.

Embodiments of the present invention can further comprise a plurality of discrete injections of a sample from the sample channel to the separation channel in a rapid sequence. The sequence can preferably be pseudo-random. A detector at the end of the separation channel detects the discrete injections after CE-induced overlap, which comprises mixing of at least one component from at least one of the discrete injections to another discrete injection. A processing device executes programming to deconvolute the CE-induced overlap in data collected by the detector so that a spectrum can be reconstructed.

Some embodiments of a microchip CE system can further comprise a plurality of CE channels within the separation channel as well as a manifold within the separation channel distributing one or more discrete injections among the plurality of CE channels. Preferably, an electrospray ionization (ESI) emitter is connected at the end of each CE channel.

In some embodiments, liquid chromatography (LC) separation is performed in conjunction with CE separation. Accordingly, the microchip CE system can further comprise a LC column connected to the sample channel and providing LC separation prior to injection into the separation channel.

Embodiments of the present invention also include methods for analyzing a sample having a plurality of components using microchip CE. In a particular embodiment, the method includes the steps of applying a sample pressure in the sample channel greater than the sample pressure in a separation channel. The sample channel is connected to the separation channel at an intersection and lacks electrodes associated with electrokinetic-based injectors. A continuous electric field for CE separation is applied along the separation channel. Injection of the sample occurs by mechanically opening for a duration a mechanical valve, not an electrokinetic-based injector. The mechanical valve is located in the sample channel or at the intersection. The electric field in the separation channel can then separate the components in the injection.

The method can further comprise repeating the mechanical opening in a rapid, pseudo-random sequence to provide a plurality of discrete injections of the sample from the sample channel to the separation channel. CE-induced overlap can be the result of mixing at least one component from at least one of the discrete injections with another discrete injection. The discrete injections are then detected at the end of the separation channel after CE-induced overlap. Finally, the CE-induced overlap in data collected by the detector is deconvoluted so that a spectrum can be reconstructed.

Alternatively, the method can further include distributing one or more injections among a plurality of CE channels within the separation channel. In preferred embodiments, an electrospray can be generated at the end of each CE channel.

In another embodiment, LC separations can be performed in conjunction with the CE separations. Accordingly, the method can further comprise separating the sample in a liquid chromatography column prior to providing an injection to the separation channel.

The purpose of the foregoing abstract is to enable the United States Patent and Trademark Office and the public generally, especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

Various advantages and novel features of the present invention are described herein and will become further readily apparent to those skilled in this art from the following detailed description. In the preceding and following descriptions, the various embodiments, including the preferred embodiments, have been shown and described. Included herein is a description of the best mode contemplated for carrying out the invention. As will be realized, the invention is capable of modification in various respects without departing from the invention. Accordingly, the drawings and description of the preferred embodiments set forth hereafter are to be regarded as illustrative in nature, and not as restrictive.

DESCRIPTION OF DRAWINGS

Embodiments of the invention are described below with reference to the following accompanying drawings.

DETAILED DESCRIPTION

The following description includes the preferred best mode of one embodiment of the present invention. It will be clear from this description of the invention that the invention is not limited to these illustrated embodiments but that the invention also includes a variety of modifications and embodiments thereto. Therefore the present description should be seen as illustrative and not limiting. While the invention is susceptible of various modifications and alternative constructions, it should be understood, that there is no intention to limit the invention to the specific form disclosed, but, on the contrary, the invention is to cover all modifications, alternative constructions, and equivalents falling within the spirit and scope of the invention as defined in the claims.

Figure 1A:
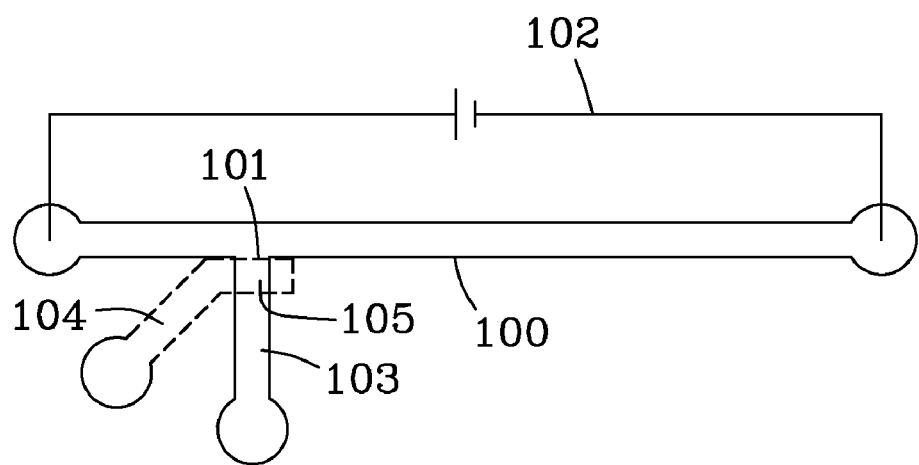
FIG. 1 includes diagrams of a microchip CE system according to one embodiment of the present invention.

FIGS. 1-9 show a variety of embodiments and aspects of the present invention. Referring first to FIG. 1, diagrams of one embodiment of a mechanical valve separating two channels in a microchip CE system are shown. FIG. 1A shows the outline of the microchip structure, which is comprises two layers. A flow layer (solid line) contains a CE separation channel 100 and a sample channel 103 with a T-shaped intersection 101. The separation channel has electrodes for applying voltages 102 associated with CE, but the electrodes are not configured for electrokinetic injection. The sample channel does not have electrodes, thereby precluding electrokinetic injection.

The control layer (dashed line) contains a microchannel 104 for valving. An exemplary, but not limiting, width for the channels is 100 μm. Exemplary lengths for the separation and sample channels are 3 cm and 0.5 cm, respectively. The channel 104 on the control layer crosses over the sample injection channel 103 and, therefore, the area at the T-shaped intersection 101 is 100 μm×100 μm and is large enough for a mechanical injector comprising a pneumatic valve 105. The pneumatic valve includes a thin elastomer membrane formed between the two layers. When a pressure is applied in the control channel, the membrane separating the two channels deforms into the flow channel to seal the sample channel (i.e., closed valve). When the pressure is released, the membrane recovers to the original state to open the valve.

Figure 1B:
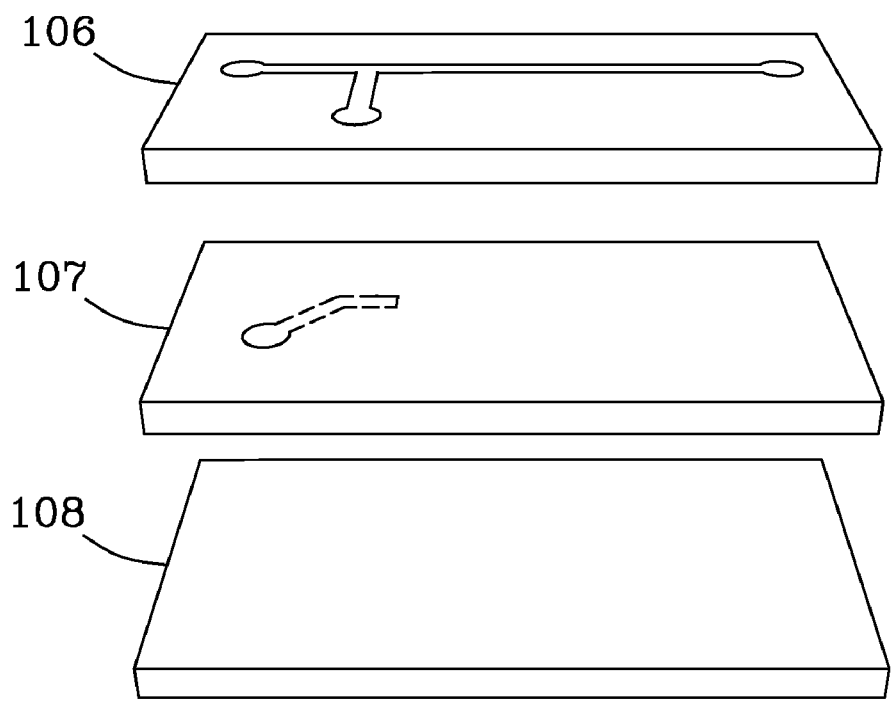

Integrated poly(dimethylsiloxane) (PDMS) microchips were fabricated using multilayer soft lithography techniques. First, two kinds of silicon templates were produced using standard photolithographic patterning. The silicon template for the control layer 107 was modified with hexamethyldisilazane (HMDS) using gas phase deposition method in order to assist in releasing the PDMS membrane from the patterned template. A 10:1 weight ratio of PDMS base monomer to curing agent was then mixed, degassed under vacuum, poured onto the patterned wafer for the flow layer 106 to a thickness of 1-2 mm and spin-coated on the surface-modified wafer at 2000 rpm for 30 s to coat the control layer to a thickness of ~50 μm, and cured in an oven at 75° C. for 2 h. After removing the patterned PDMS with flow channels from the template, a small through-hole was created at the end of sample injection channel by punching the substrate with a manually sharpened syringe needle. Two holes were generated at the ends of separation channel for connections to buffer reservoirs. The flow layer PDMS piece was then cleaned and treated with oxygen plasma for 30 s. Immediately, it was aligned on the top of the control layer PDMS membrane (still on the silicon wafer) and assembled together to enclose the flow channel. After placing in an oven at 75° C. for 2 h to form an irreversible bond, the PDMS block containing flow and control layers was removed from the control layer silicon template, a hole was punched at the end of the control channel, and the substrate was finally bonded to an unpatterned PDMS piece 108 to enclose the control channel using oxygen plasma treatment. An expanded view of the three layers 106, 107, and 108 composing the assembled channels and valve is illustrated in FIG. 1B.

In the present example, polyE-323 was used to coat the PDMS microchannel surfaces to provide anodic EOF in the same direction as electrophoresis for the negatively charged analytes. PolyE-323 is a cationic polyamine, which can be absorbed on negatively charged surfaces through strong electrostatic interaction. The polymer can support strong and stable anodic electroosmotic flow (EOF). To reduce analyte adsorption onto the modified surface resulting from the electrostatic interaction, all samples were prepared in a buffer solution containing 0.5% HPC. Briefly, the PolyE-323 was synthesized by mixing 17.65 g 1,2-bis(3-aminopropylamino)ethane with 20 g water and 9.3 g epichlorohydrine by strong stirring. Two days later, 100 g water was added and the reaction was allowed to continue for 1 week at room temperature. The polymer solution (5 mL) was then diluted in 25 mL of 0.2 M acetic acid, adjusting the pH to ~7. The diluted polymer solution was filtered using 0.2 μm syringe filters and stored at 4° C.

During the 2 h following the PDMS microchip assembly with oxygen plasma treatment, the diluted polyE-323 solution was pumped into the separation channel through the sample introduction hole for 10 min, and then the solution was left in the channel for 30 min. The channel was then flushed with 10 mM ammonium acetate (pH 7) for 10 min to remove excess polymer. Finally, the microchip was filled with a run buffer (10 mM carbonate buffer, pH 9.3) for CE separation.

Figure 2:
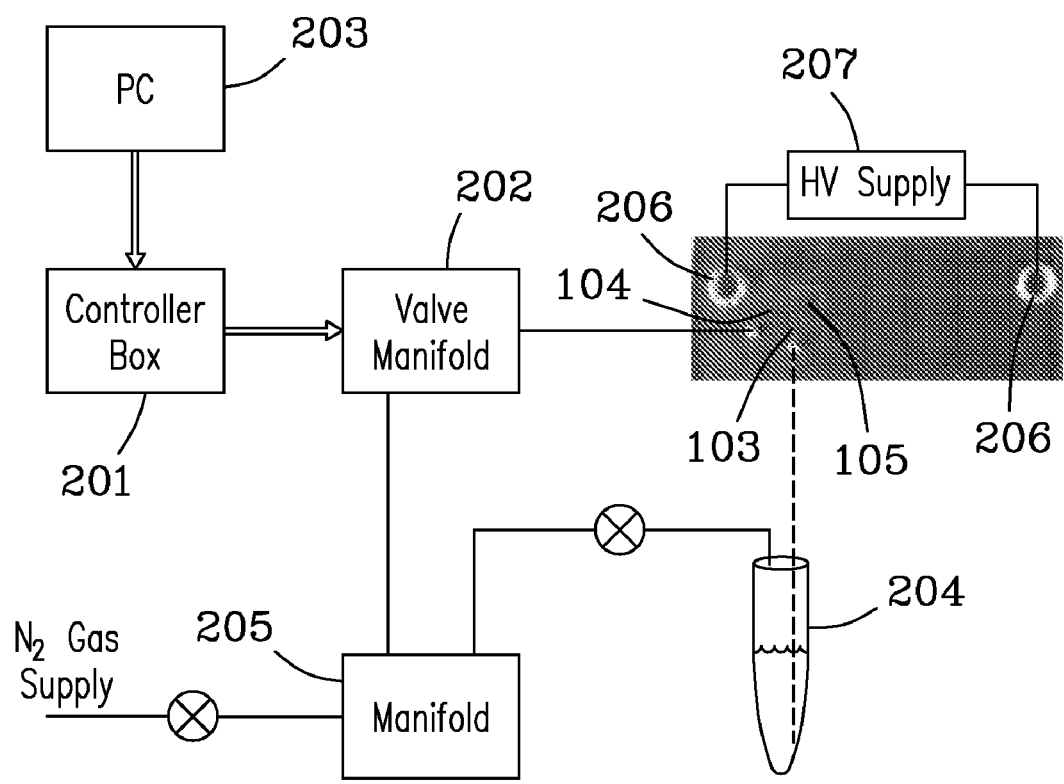
FIG. 2 is a diagram depicting a microchip CE system using pressure injection and a pneumatic valve according to one embodiment of the present invention.

FIG. 2 shows a diagram depicting a microchip CE system using pressure injection with the pneumatic valve described above. The valve control sub-system comprises a valve manifold 202 and a controller box 201 controlling the valve manifold. The valve manifold was connected to a second manifold 205 having manually controlled outputs. The second manifold was connected with a regulated continuous $N_2$ gas pressure supply. One output of the valve manifold was connected to the on-chip control line 104 with a tube to provide pneumatic operation and control of the valve. The pneumatic valve 105 was operated and controlled automatically through a personal computer (PC) 203. The valve actuation time and frequency were set in the software. The valve control channel in the PDMS device can be filled with either water or air, but water was generally used to avoid introduction of bubbles into the flow channels. The sample was contained in a sealed vial 204 with an air inlet to pressurize the sample and an outlet allowing sample to be transferred into the microchannel through a fused-silica capillary. One end of the capillary was immersed into the liquid sample and the other end was inserted into a ~2 mm long section of Tygon tubing, which was then inserted into the through-hole of the sample injection channel 103 on the microchip. Before injection, any air bubbles trapped in the transfer line and microchannel were removed. For performing microchip CE separation, a high voltage (typically, 3 kV) was continuously applied along the separation channel 100 using a high-voltage power supply 207 via platinum electrodes 206 placed in the reservoirs. The pneumatic valve was actuated to inject discrete sample plugs into the separation channel for subsequent CE separation.

A laser-induced fluorescence (LIF) system was employed for detection. Briefly, a 488-nm line from an air-cooled Ar ion laser was passed into an inverted optic microscope and the fluorescence was collected using a CCD camera. For imaging experiments, a mercury lamp was used as the light source and the fluorescence was collected with a digital camera.

Figure 3:
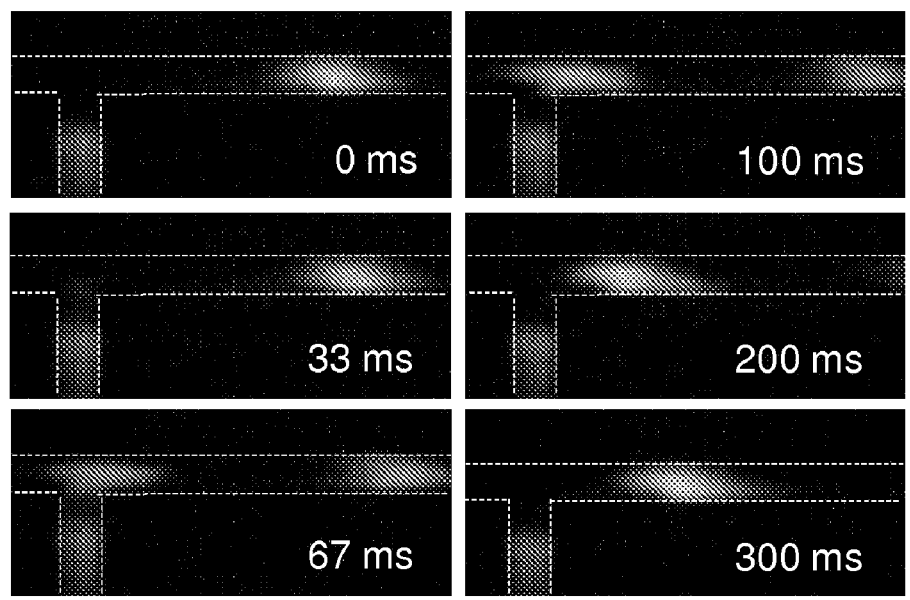
FIG. 3 is a sequence of micrographs depicting one cycle of sample injection.

FIG. 3 is a sequence of micrographs depicting one cycle of sample injection controlled by the pneumatic valve embodiment described above. The sample injection pressure was 1.5 psi and the valve actuation time and frequency were 33 ms and 2.2 Hz, respectively. The valve control pressure was 30 psi. The microchannel surface was dynamically coated with PolyE-323 and an electric field of 1000 V/cm was applied along the separation channel. When a negatively charged fluorescein sample plug was injected into the separation channel, the plug migrated downstream to the anode immediately because the electrophoresis of analyte and the electroosmotic flow (EOF) were in the same direction. While the sample plugs in the micrographs exhibit minor blurring due to molecular diffusion effects, there is minimal negative impact on the separation. The injected sample volume shown in FIG. 3 is approximately 270 pL based on the plug shape and the microchannel dimensions.

Figure 4A:
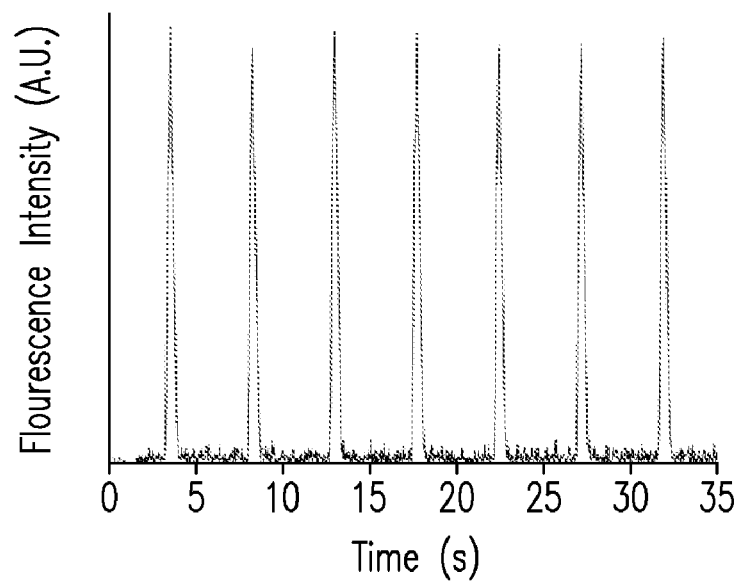
FIG. 4 includes graphs of fluorescence intensity as a function of time for four repeatable injection results at frequencies of 0.21 Hz, 0.43 Hz, 1.1 Hz, and 2.2 Hz, respectively.
Figure 4B:
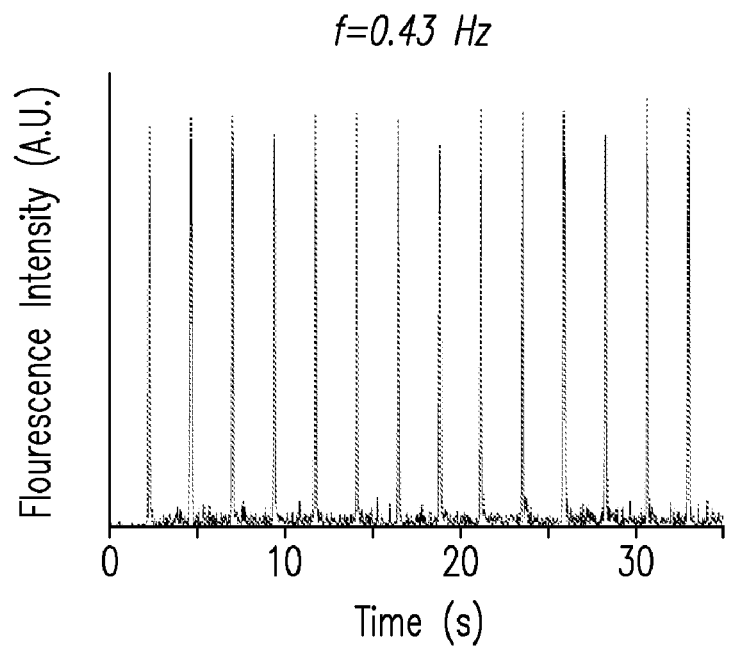
Figure 4C:
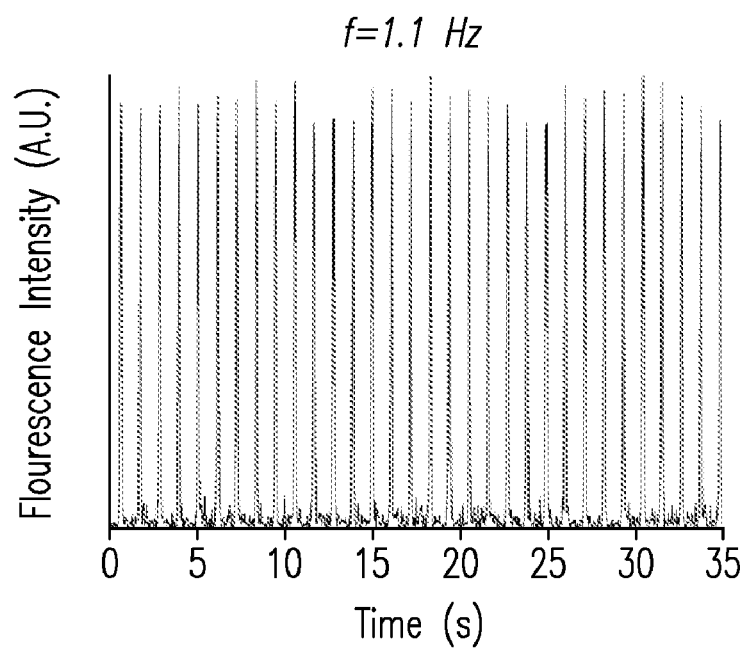
Figure 4D:
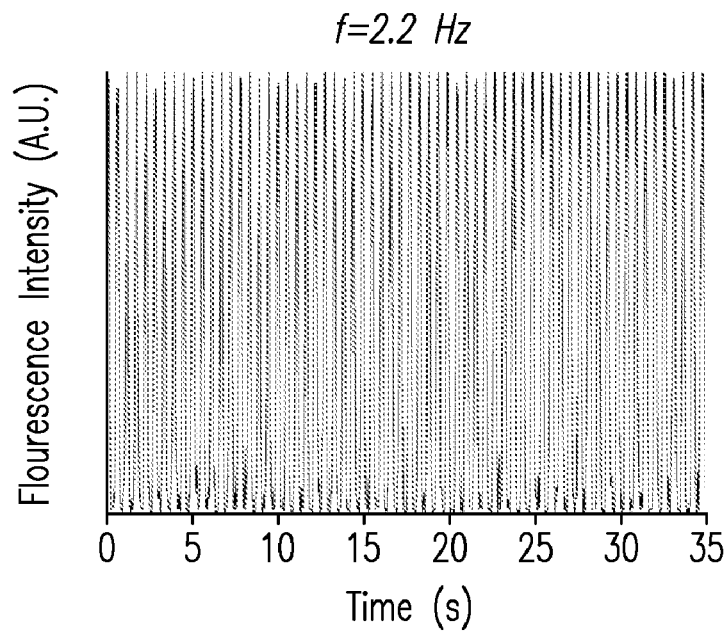

In one embodiment, the sample injection can be operated at different frequencies in the present injection mode. FIG. 4 shows four repeatable injection results at frequencies of 0.21 Hz, 0.43 Hz, 1.1 Hz, and 2.2 Hz, respectively. The fluorescence intensity was recorded close to the T intersection. The relative standard deviations (RSD) of the peak height and width shown in FIG. 4 are listed in Table 1, which indicates good reproducibility has been achieved for repeated injections with RSD less than 3.6%. In all tests, the valve actuation time was the same (33 ms). In FIG. 4A, broader peaks were obtained as the valve control and sample injection pressures were set at 20 psi and 2 psi, respectively, and the injected sample volume was approximately 500 pL. In FIGS. 4B and 4C, the valve control and sample injection pressures were 30 psi and 1 psi, respectively. In FIG. 4D, the valve control and sample injection pressures were set at 30 psi and 1.5 psi, respectively.

TABLE 1

Relative standard deviation (RSD) of the peak height and width shown in FIG. 4.

|  | A | B | C | D |
|---|---|---|---|---|
| RSD of peak height | 1.8% | 2.9% | 3.4% | 1.8% |
| RSD of peak width | 3.4% | 3.6% | 3.3% | 3.6% |

The pressure-injected sample volume can depend on several factors, including the mechanical injector open time, sample injection pressure, and the backpressure present in the separation channel. The mechanical injector open time is determined by the actuation time, the valve control pressure, and the mechanical properties of the injector (e.g., the PDMS membrane in the pneumatic valve described previously). FIG. 5 depicts the relationships between those parameters and the peak width of injected fluorescein samples. Here, the peak width was recorded at approximately 400 μm downstream of the intersection to represent the original injected sample plug size and minimize the influence of the plug migration in the channel and diffusion. All data shown were collected from the same pneumatic valve device.

Figure 5A:
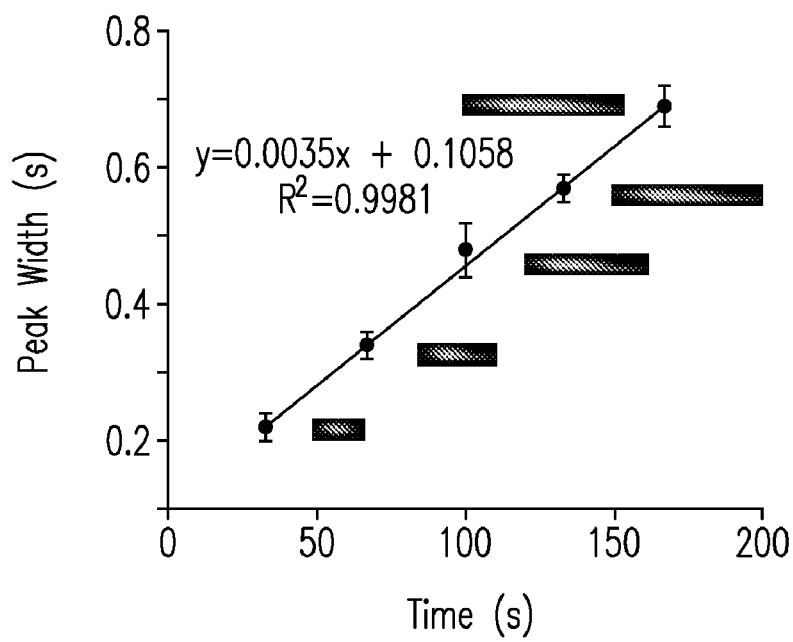
FIG. 5 includes graphs of peak width as a function of various operating parameters.

FIG. 5A shows that the peak width increases linearly with the valve actuation time, because the valve was opened for a longer period of time allowing more sample to enter into the separation channel. In this experiment, the sample injection pressure was 1 psi and the valve control pressure was 30 psi. The valve actuation frequency was 0.21 Hz. Valve actuation times ranging from 33 ms to 167 ms were investigated. The insets are the pictures of the injected fluorescein sample plugs corresponding to different valve actuation times. Based on the length of the sample plugs and the dimension of the channel, the injected sample volumes were estimated from less than 200 pL to approximately 1 mL. Longer actuation time (>200 ms) was not tested because the injected sample plug would be too long to achieve good separation performance. But it is feasible to change the microchannel dimension, by for example, increasing the separation channel depth, to achieve desirable injected sample volume without increasing plug length.

Figure 5B:
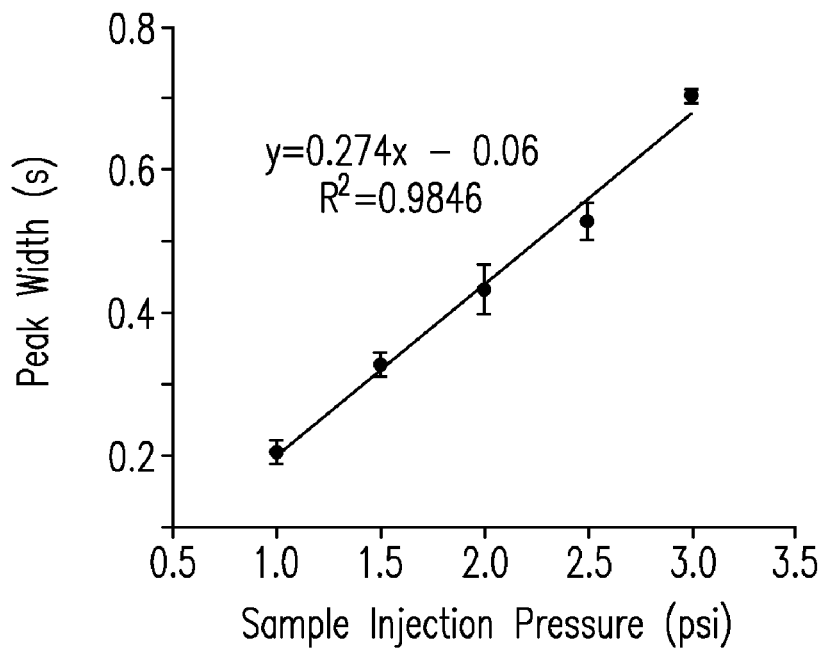

Similarly, the peak width increases with the sample injection pressure (FIG. 5B). As the injection pressure increased, more samples were pressurized into the separation channel when opening the valve because the sample flow rate increased. Here, the valve actuation time (33 ms) and frequency (0.21 Hz) were set constant, and the valve control pressure was 30 psi. Only low injection pressures (1-3 psi) were investigated. When higher injection pressure was applied, the pulsed hydrodynamic flow induced in the separation channel and the longer injected sample plug would destroy the separation. Furthermore, the higher injection pressure increased the back pressure present in the sample channel, increasing the resistance to closing the valve. For example, the fitting line based on the first four points in FIG. 5B shows a linear relationship ($R^2$=0.997). But the fifth point (3 psi) slightly deviates to the upside of the fitting line, which indicates that valve open time is much longer under this pressure.

Figure 5C:
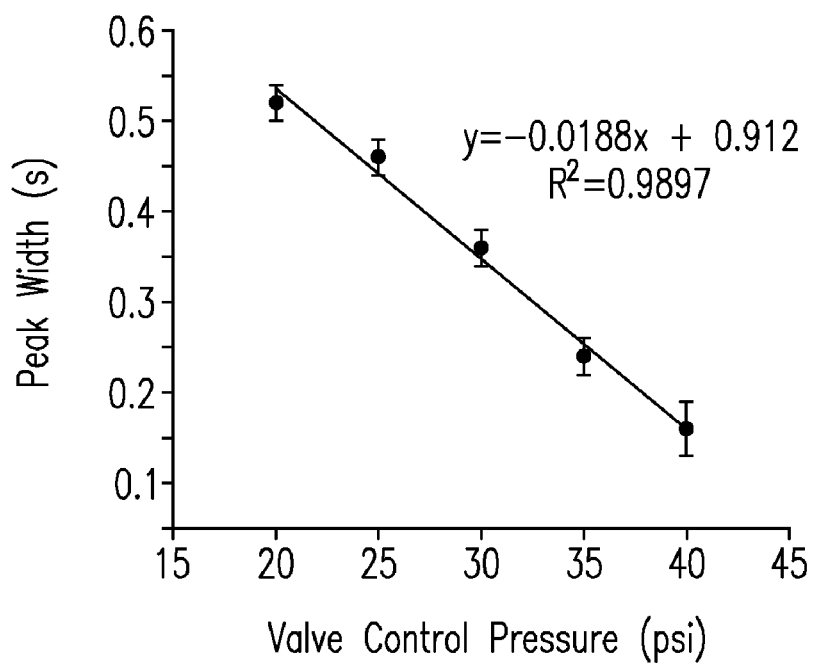

FIG. 5C shows that the peak width linearly decreases with increase in the valve control pressure. During this investigation, the valve actuation time (33 ms) and frequency (0.21 Hz) and the sample injection pressure (1.5 psi) were kept constant. Valve control pressure was tested from 20 psi to 40 psi. When the pressure was lower, the response of the PDMS membrane to the pressure was slow because of its flexibility. Therefore, it took a longer time to close the valve. This behavior resulted in actual valve open times that were much longer. If the pressure was too low (<20 psi), sample leakage occurred or the injected sample plug was too long, because the valve was not completely closed after actuation. When applying relatively higher control pressures, the PDMS membrane can stick on the channel surface and can take additional time to relax, and then open the valve. On the other hand, the PDMS membrane responds quickly to the pressure to close the valve. Thus, the actual time for the valve to reach the open state can still be shorter. If the pressure was too high, the PDMS membrane can stick to the channel surface too tightly and can take a very long time to open the valve or the valve may not even open during the valve actuation period. In some instances, pressures greater than 40 psi were too high.

Figure 5D:
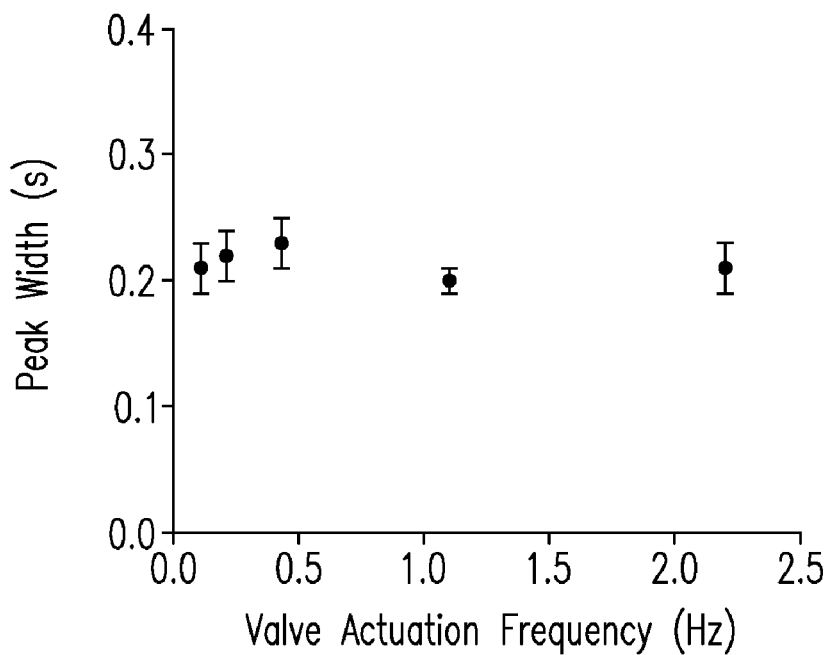

FIG. 5D shows that the injected sample plug size is independent of the valve actuation frequency. In these series of tests, the sample injection pressure was 1 psi, the valve actuation time was 33 ms, and the valve control pressure was 30 psi. Because both the sample and the run buffer were diluted aqueous solutions, the variance of the backpressure present in the separation channel was negligible. The injected sample plug size varied little at different valve actuation frequencies.

Figure 6:
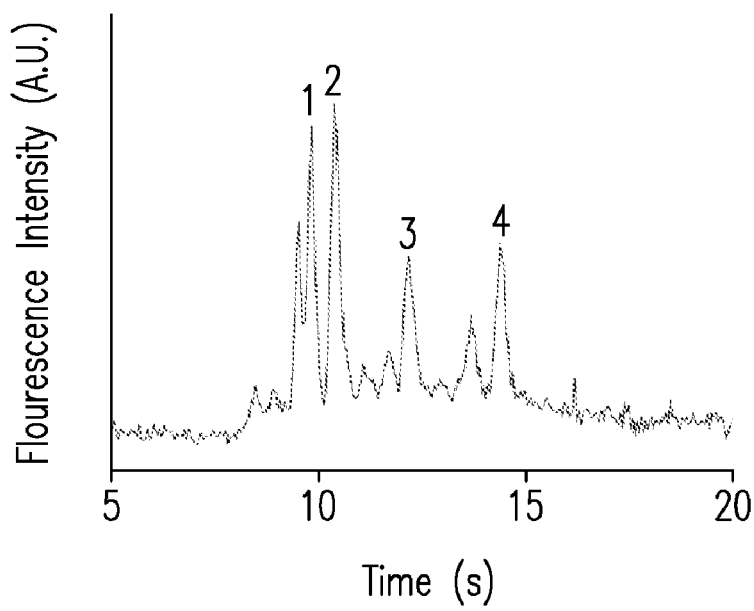
FIG. 6 is a graph of fluorescence intensity as a function of time and shows a CE separation of four FITC-labeled amino acids using embodiments of the present invention.

FIG. 6 shows a CE separation of four FITC-labeled amino acids using embodiments of the present invention. The sample concentration of each amino acid was 250 nM. The valve actuation time and frequency were set as 67 ms and ~0.1 Hz. The sample injection and valve control pressures were 3 psi and 40 psi, respectively. When the valve was actuated, the data acquisition system was activated to record the fluorescence intensity at the end of the separation channel. The analyte migration distance was measured as approximately 2.4 cm. Only the first cycle of separation was shown in FIG. 6. Four major peaks were completely resolved in 15 s, and some minor peaks showed up due to the impurities present in the sample solution. The theoretical plate numbers of each major peak are calculated and listed in Table 2. The efficiency of the separation is higher than $9.2 \times 10^3$ plates for ~2.4 cm long microchannel.

TABLE 2

Figure 7:
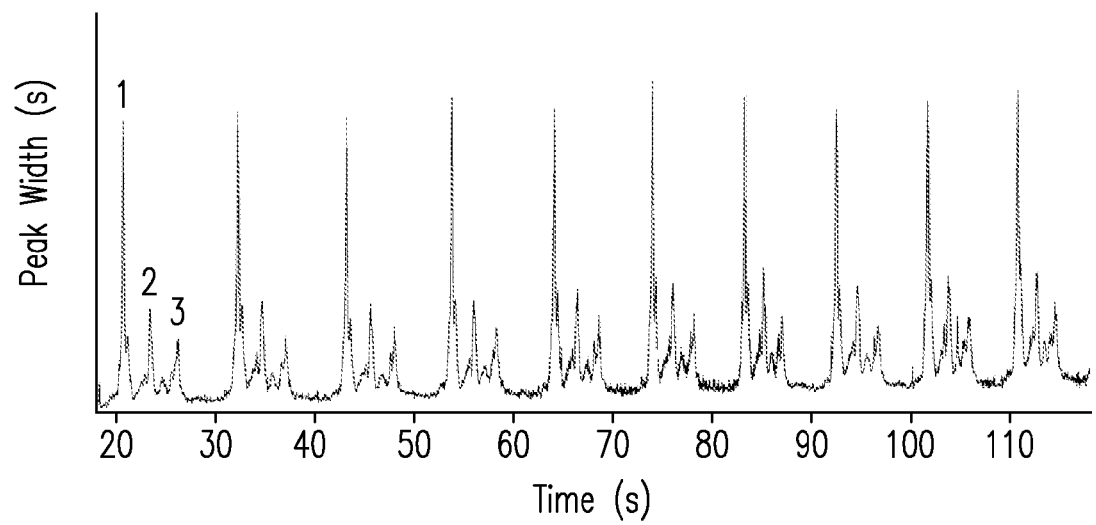
FIG. 7 is a graph showing repeated CE separation of three FITC-labeled amino acids.

Theoretical plate numbers of each peak shown in FIGS. 6, 7 and 8.

Figure 8A:
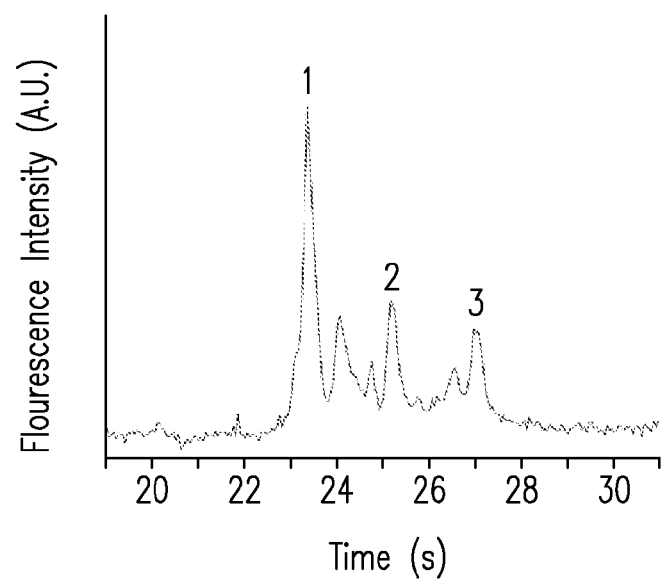
FIG. 8 includes graphs showing portions of FIG. 7 in greater detail.
Figure 8B:
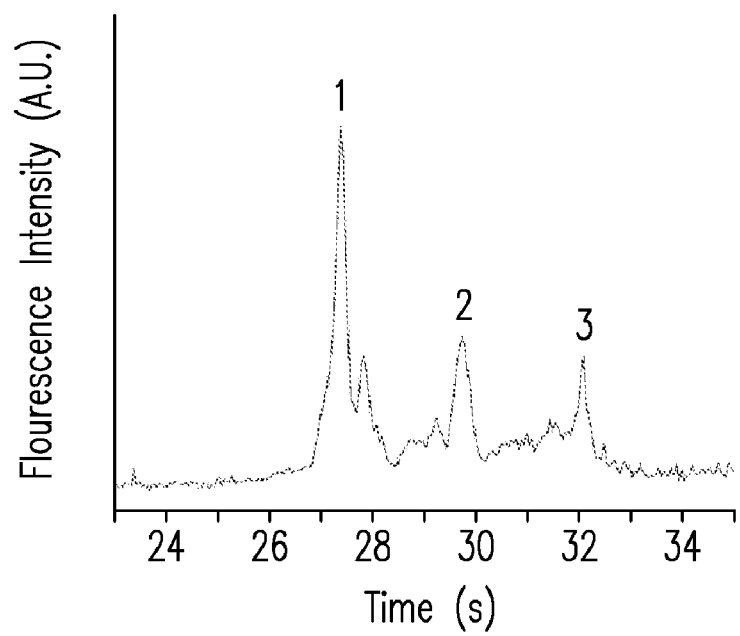
Figure 8C:
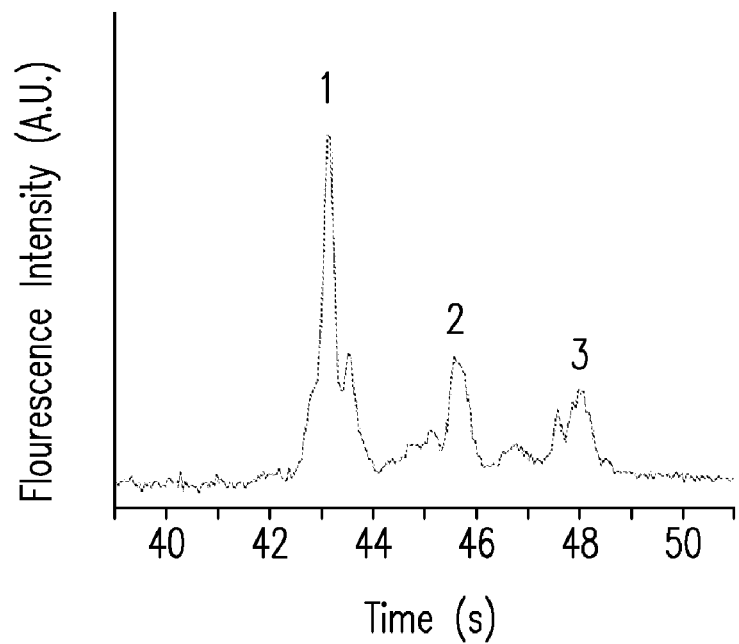
Figure 9:
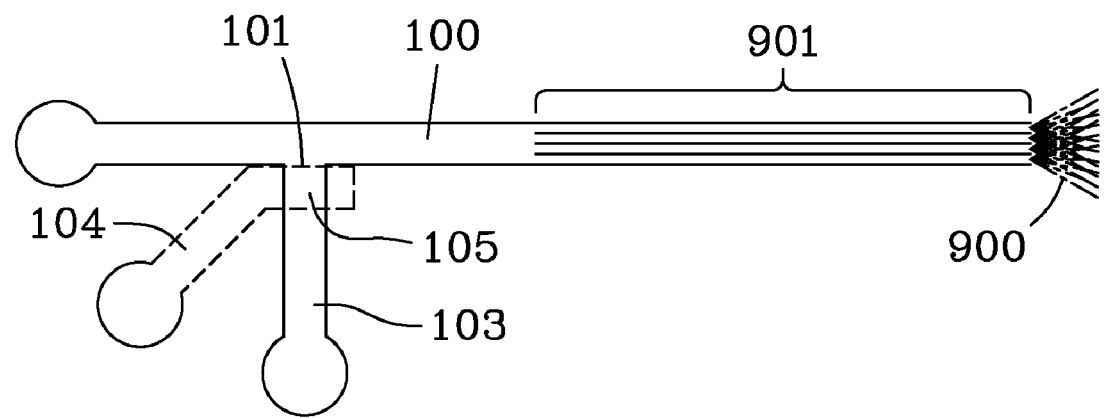
FIG. 9 is a diagram depicting one embodiment in which the separation channel comprises a plurality of CE channels.

|  | 1 | 2 | 3 | 4 |
|---|---|---|---|---|
| FIG. 6 | $1.3 \times 10^4$ | $9.6 \times 10^3$ | $9.2 \times 10^3$ | $1.3 \times 10^4$ |
| FIG. 7 | $(8.8 \pm 0.5) \times 10^3$ | $(7.5 \pm 0.4) \times 10^3$ | $(8.5 \pm 1.0) \times 10^3$ | |
| FIG. 8A | $7.4 \times 10^3$ | $1.0 \times 10^4$ | $1.3 \times 10^4$ | |
| FIG. 8B | $7.7 \times 10^3$ | $8.3 \times 10^3$ | $1.6 \times 10^4$ | |
| FIG. 8C | $9.0 \times 10^3$ | $7.0 \times 10^3$ | $7.6 \times 10^3$ | |

FIG. 7 shows a repeated CE separation of three FITC-labeled amino acids. Although only 100-second period of separation (10 runs) is shown, the data was recorded after running the microchip continuously for ~2 h, corresponding to more than 700 runs. The average separation efficiency for each peak is listed in Table 2. Compared with the separation shown in FIG. 6, the efficiencies obtained in FIG. 7 decreased slightly due to some degradation of the PolyE-323 dynamic coating during the preceding hours of operation. However, the efficiency was higher than $2.9 \times 10^5$ plates/m. It should be pointed out that the peak positions at time scale were not the real peak migration times. The migration times of each peak can be estimated based on the intervals between injections and the first valve actuation time.

FIG. 8 shows portions of FIG. 7 in greater detail. FIGS. 8A and 8B show the same separations performed earlier. Based on the recording time, if the separation shown in FIG. 8A is defined as the first one, the separation in FIG. 8B is approximately the $40^{th}$ run, and the separation in FIG. 8C is about the $100^{th}$ run. It should be noted that all three separations are randomly selected to evaluate the pressure injection and microchip separation performance. All peak efficiencies are listed in Table 2. Apparently, the separation is reproducible although the separation becomes slightly worse with increase in the operation time, which is a normal phenomenon because of the dynamically coated surface.

One advantage of pressure-based injection method is a lack of injection bias, which can be evaluated based on the separations shown in FIGS. 7 and 8. We calculated the peak area ratios based on the first peak displayed in each cycle of separation (Table 3). For each peak, the values only fluctuate slightly but appear stable, which indicates that no sample bias is observed in the pressure injection. On the contrary, the values changed approximately 2 times in 20 runs for electrokinetic injection method reported previously.

TABLE 3

Evaluation of the peak area ratios shown in FIGS. 7 and 8.

| peak area ratio | FIG. 7 | FIG. 8A | FIG. 8B | FIG. 8C |
|---|---|---|---|---|
| S2/S1 | 44 ± 3% | 42% | 46% | 44% |
| S3/S1 | 34 ± 3% | 33% | 34% | 37% |

*S1, S2 and S3 represent the peak areas of $1^{st}$, $2^{nd}$ and $3^{rd}$ peak, respectively, indicated in the Figures.

The fast, reproducible sample injections described above provide for multiplexed CE, in which separations from multiple injections overlap in the separation channel and are subsequently analyzed in comparison and in combination. The multiplexed CE separation can provide an increase in signal-to-noise ratio and a much higher duty cycle compared with discrete CE separations. In some embodiments, multiplexed CE is coupled with LC separations for two dimensions of orthogonal liquid phase separations, and for providing a much greater peak capacity without significant increase in the analysis time. Generally, LC-CE has not been practical using electrokinetic injection, as the low sampling rate and the long delay time required between injections has led to almost all of the sample from the LC column being wasted. The combination of the fast injections and the multiplexed CE can utilize at least 50% of the LC eluent for high-sensitivity, high-peak capacity analyses.

In a preferred embodiment, LC is coupled to fast, multiplexed microchip CE separations followed by high-performance electrospray ionization-mass spectrometry (ESI-MS). Accordingly, a LC column is connected to the sample channel, which provides a plurality of sample injections to the separation channel through a sample injector. The sample injector can include the pneumatic valve describe elsewhere herein or another mechanical valve providing fast, reproducible sample injections without the use of electrokinetic techniques. The separation channel terminates in one or more ESI emitters directed at a mass spectrometer. This configuration can provide at least a 5-fold increase in proteome coverage for complex samples relative to a comparable LC-MS platform alone.

The pressure differential between the sample channel and the separation channel is such that upon briefly opening the mechanical valve, analyte is rapidly introduced for separation. A potential is continuously applied in the separation channel enabling automatic separation of the sample injection. Preferably, the plurality of rapid injections occurs in a pseudorandom sequence resulting in multiple overlapping separations, which can be deconvoluted to reconstruct a spectrum. Deconvolution can be achieved according to a modified Hadamard transform. The achievable gain in signal-to-noise ratio relative to simple signal averaging can be proportional to the square root of the number of injections.

As mentioned elsewhere herein, one challenge in coupling LC and CE separations is the disparity in sample flow rates associated with each technique. LC typically requires higher flow rates by orders of magnitude. Accordingly, referring to FIG. 9, a preferred embodiment of the present invention includes a single pneumatic injector that spans multiple CE channels 901 within the separation channel 100. When coupled with LC, the eluent from the LC column can be provided as a relatively large sample injection by the sample injector and can be distributed among a plurality of CE channels. In one instance, twenty or more CE channels can exist within the separation channel. Generally, the injection volume can be increased in direct proportion with the number of CE channels, enabling high resolution separations while processing sample volumes compatible with typical nanoLC flow rates (e.g., 100-500 mL/min).

Preferably, each CE channel will terminate with an electrospray 900 at its own ESI emitter. The array of emitters can provide an order of magnitude sensitivity improvement relative to a single emitter analysis. The enhanced sensitivity, in combination with the greater than ten-fold gain in peak capacity relative to the equivalent LC separation alone can lead to significantly improved dynamic range, more quantitative ionization, and greatly increased sample identifications.

While a number of embodiments of the present invention have been shown and described, it will be apparent to those skilled in the art that many changes and modifications may be made without departing from the invention in its broader aspects. The appended claims, therefore, are intended to cover all such changes and modifications as they fall within the true spirit and scope of the invention.

We claim:

1. A method for analyzing a sample by microchip capillary electrophoresis, the method characterized by the steps of:

Applying a sample pressure in a sample channel greater than the sample pressure in a separation channel, the sample channel being connected to the separation channel at an intersection and lacking electrodes associated with electrokinetic-based injectors;

Applying a continuous electric field for CE separation along the separation channel;

Mechanically opening for a duration a mechanical valve, not an electrokinetic-based injector, located in the sample channel or at the intersection with the separation channel, thereby providing an injection of the sample from the sample channel into the separation channel, the injection volume being a function of the duration;

Separating sample components in the injection according to the electric field applied in the separation channel;

Repeating said mechanically opening in a rapid, pseudo-random sequence, thereby providing a plurality of discrete injections of the sample from the sample channel to the separation channel, the sample comprising a plurality of components;

Mixing at least one component from at least one of the discrete injections to another discrete injection, thereby resulting in CE-induced overlap;

Detecting the discrete injections at the end of the separation channel after the CE-induced overlap; and Deconvoluting the CE-induced overlap.

2. The method of claim 1, further comprising distributing the injection among a plurality of CE channels within the separation channel.

3. The method of claim 2, further comprising generating an electrospray at the end of each CE channel.

4. The method of claim 1, further comprising separating the sample in a liquid chromatography column prior to said providing an injection to the separation channel.

* * * * *